United States Patent [19]

McDavid et al.

[11] Patent Number: 4,805,122
[45] Date of Patent: Feb. 14, 1989

[54] TEMPERATURE CONTROL SYSTEM FOR CUNTANEOUS GAS MONITOR

[75] Inventors: Larry S. McDavid, Anaheim; Michael Pawlowski, Chino; Stuart L. Foster, Fountain Valley; Gerald T. Stillman, Fullerton, all of Calif.

[73] Assignee: Sensormedics Corporation, Anaheim, Calif.

[21] Appl. No.: 148,115

[22] Filed: Jan. 25, 1988

Related U.S. Application Data

[63] Continuation of Ser. No. 948,441, Dec. 31, 1986, abandoned, which is a continuation of Ser. No. 510,149, Jul. 1, 1983, abandoned.

[51] Int. Cl.$^4$ .............. G06F 15/42; G01N 27/26; A61B 5/05
[52] U.S. Cl. .................... 364/557; 128/635; 364/580; 364/413.04; 364/413.11; 204/431
[58] Field of Search ............ 364/153, 154, 183, 184, 364/415, 417, 506, 557, 580; 128/635, 736; 374/163; 123/179 B, 179 K; 204/403, 406, 408, 431

[56] References Cited

U.S. PATENT DOCUMENTS

| | | | |
|---|---|---|---|
| 3,795,239 | 3/1974 | Eberhard et al. | 128/635 |
| 3,929,605 | 12/1975 | Lubbers et al. | 204/195 P |
| 3,985,266 | 10/1976 | Wright, Jr. | 364/180 X |
| 4,071,745 | 1/1978 | Hall | 364/557 |
| 4,167,663 | 9/1978 | Granzow, Jr. et al. | 19/497 |
| 4,197,853 | 4/1980 | Parker | 128/632 |
| 4,204,429 | 5/1980 | Shimazaki | 374/164 |
| 4,206,552 | 6/1980 | Pomerantz et al. | 364/477 |
| 4,227,535 | 10/1980 | Connor | 128/401 |
| 4,250,738 | 2/1981 | Huch | 73/15.4 |
| 4,288,854 | 9/1981 | Burroughs | 364/180 X |
| 4,334,541 | 6/1982 | Leist | 128/632 |
| 4,348,583 | 9/1982 | Bube et al. | 123/179 H X |
| 4,350,876 | 9/1982 | Kubota et al. | 123/179 B X |
| 4,386,649 | 6/1983 | Hines et al. | 364/557 |
| 4,388,692 | 6/1983 | Jones et al. | 364/557 |
| 4,391,237 | 8/1983 | Abe et al. | 123/179 H |
| 4,409,662 | 10/1983 | Rao | 364/557 |
| 4,432,365 | 2/1984 | Leist | 128/635 |
| 4,444,168 | 4/1984 | Matsumura et al. | 123/179 B |
| 4,506,145 | 3/1985 | Kawamura et al. | 123/179 H |
| 4,552,102 | 11/1985 | Egle | 123/179 H |
| 4,586,149 | 4/1986 | Stillman et al. | 374/163 X |
| 4,601,293 | 7/1986 | Foster et al. | 128/635 |
| 4,674,027 | 6/1987 | Beckey | 364/557 |

OTHER PUBLICATIONS

Eberhard et al, "A Sensor for Non Invasive Monitoring of Carbon Dioxide", *Journal of Clinical Engineering*, vol. 6, No. 1, Jan.-Mar. 1981, pp. 35-39.

"Cutaneous Blood Flow and Its Relationship to Transcutaneous $O_2/CO_2$ Measurements", A. V. Beran et al, *Critical Care Medicine*, vol. 9, No. 10, pp. 736-741 (1981).

*Primary Examiner*—Parshotam S. Lall
*Assistant Examiner*—Joseph L. Dixon
*Attorney, Agent, or Firm*—Lyon & Lyon

[57] ABSTRACT

A temperature control system for an electrically heated cutaneous gas sensor. A heating element is provided with heating current by a closed loop temperature control circuit. The system includes a plurality of temperature monitoring circuits which are arranged to turn off the flow of heating current if the temperature of the sensor takes on an unacceptable value. The system also includes temperature setting circuitry for applying an increased temperature setpoint signal to the temperature control circuit, for a predetermined time, to reduce the time delay between the application of the sensor to the patient and the production of usable sensor data. Timing circuitry assures that the flow of heating current is not turned off in response to normal sensor temperature transients.

15 Claims, 5 Drawing Sheets

TEMPERATURE CONTROL SYSTEM FOR CUTANEOUS GAS MONITOR

This is a continuation of co-pending application Ser. No. 948,441 filed on Dec. 31, 1986, now abandoned, which is a continuation of application Ser. No. 510,149, filed on July 1, 1983, now abandoned.

BACKGROUND OF THE INVENTION

The present invention relates to cutaneous gas sensors and is directed more particularly to an improved temperature control system which protects a patient from exposure to cutaneous gas sensors which are operating at execessive temperatures, and which significantly reduces the time that elapses between the application of the sensor to the patient and the generation of useful data.

Among the non-invasive patient monitoring instruments which have been developed recently is an instrument known as a cutaneous gas sensor. Gas sensors of this type make use of known gas detection techniques to measure the partial pressure of a gas, such as oxygen or carbon dioxide, which diffuses outwardly through the pores of a patient's skin. Cutaneous gas sensors have also been developed which simultaneously measure the partial pressure of both oxygen and carbon dioxide. One cutaneous gas sensor of the latter type is described in "Cutaneous Blood Flow and its Relationship to Transcutaneous $O_2/CO_2$ Measurements", by A. V. Beran, et al., "Critical Care Medicine", Vol. 9, No. 10, pp. 736–741 (1981).

Because the rate at which blood gases diffuse through human skin is related to the temperature of the skin, cutaneous gas sensors include heating elements whereby the temperature of the skin at the measurement site may be maintained at a temperature that is higher than normal body temperature. A typical gas sensor will, for example, be maintained at a temperature, such as 42° to 43° C., which is several degrees higher than the normal human body temperature of 37° C. This elevated temperature is maintained by a closed loop temperature control circuit which continuously compares the actual sensor temperature with a desired setpoint temperature and increases or decreases the current flow through the heating element as necessary to maintain the desired temperature.

Existing temperature control circuits for cutaneous gas sensors have two important deficiencies which limit their usefulness. One of these is that temperature control circuits lack adequate provision for shutting off the flow of current through the heating element in the event that one or more parts of the circuit malfunction. Such a shutoff is extremely important because cutaneous gas sensors are often applied to patients, such as infants or comatose individuals, who are unable to remove a gas sensor the control circuitry of which has failed in a way that causes it to apply excessive current to the heating element. This excessive current can result in serious injury, particularly in cases in which gas sensors are allowed to operate unattended for hours at a time.

If, as is often the case, the gas sensor operates under the control of a programmed microcomputer, the solution to the problem of automatically shutting off the flow of heater current is made more difficult by the fact that microcomputers can malfunction as a result of power line transients, electrical noise and cosmic rays. In some cases, these malfunctions can cause the microcomputer to become unable to limit the flow of heater current, or even to initiate the flow of excessive heater current.

Another deficiency of presently available cutaneous gas sensors is that they take a long time to come into thermal equilibrium with a patient after first being applied thereto. When, for example, a sensor at a temperature of 42° C. is first applied to a patient whose body is at a temperature of 37° C., the temperature of the part of the patient to which the sensor is applied (the measurement site) will initially remain below the temperature at which useful data can be taken. This condition will continue until enough additional power can be applied to the heater to raise the temperature of the measurement site to 42° C. Since the amount of power supplied to the sensor depends upon the difference between the actual and desired temperature of the measurement site, the power supplied to the heater is gradually reduced as the temperature of the measurement site approaches 42° C. As a result, the temperature of the measurement site tends to approach the desired value in an asymptotic manner. During this asymptotic approach, 30 minutes or more may pass between the time that the sensor is first applied and the time that useful data can be produced.

SUMMARY OF THE INVENTION

In accordance with the present invention there is provided improved temperature control circuitry which does not exhibit either of the above-described deficiencies.

In accordance with one important feature of the present invention there is provided a closed loop temperature control system which includes a plurality of independently operating circuits for protecting a patient from being burned by gas sensors which have begun to operate at excessive temperatures. In the preferred embodiment, the temperature control system includes both hard-wired and programmable temperature monitoring circuits, either of which can shut off the flow of power to the sensor when the temperature of the sensor takes on an unacceptable value. In addition the temperature control system includes circuitry for monitoring the operation of the programmable temperature monitoring circuit and for shutting off the flow of heating power to the sensor when it determines that the latter circuit has or may have malfunctioned. Together, these circuits provide a patient with in-depth protection against burns resulting from circuit malfunctions or other out of limit conditions.

In accordance with another important feature of the present invention, the temperature control system includes circuitry for raising the setpoint temperature of the system above its normal value, for a predetermined time, each time that the sensor is first applied to a patient. By increasing the rate at which power is supplied to the sensor, this circuitry causes the temperature of the measurement site to rise to the desired value in a non-asymptotic manner. As a result, the sensor is able to provide useful data within a fraction of the time required by previously used temperature control systems.

In accordance with still another important feature of the present invention, the temperature control system of the invention is so designed that, without jeopardizing the safety of the patient, the temperature monitoring circuits are prevented or inhibited from shutting down the system during normal transients of the type which occur as a result of the start up of the system or as a result of changes in the temperature setpoint. During the time that this inhibited condition exists, the system retains the ability to protect the patient against unsafe sensor temperatures. Thus, the system is able to combine flexible temperature control with a high level of patient protection.

DESCRIPTION OF THE DRAWINGS

Other objects and advantages of the present invention will be apparent from the following description and drawings in which.

DESCRIPTION OF THE PREFERRED EMBODIMENT

Figure 1:
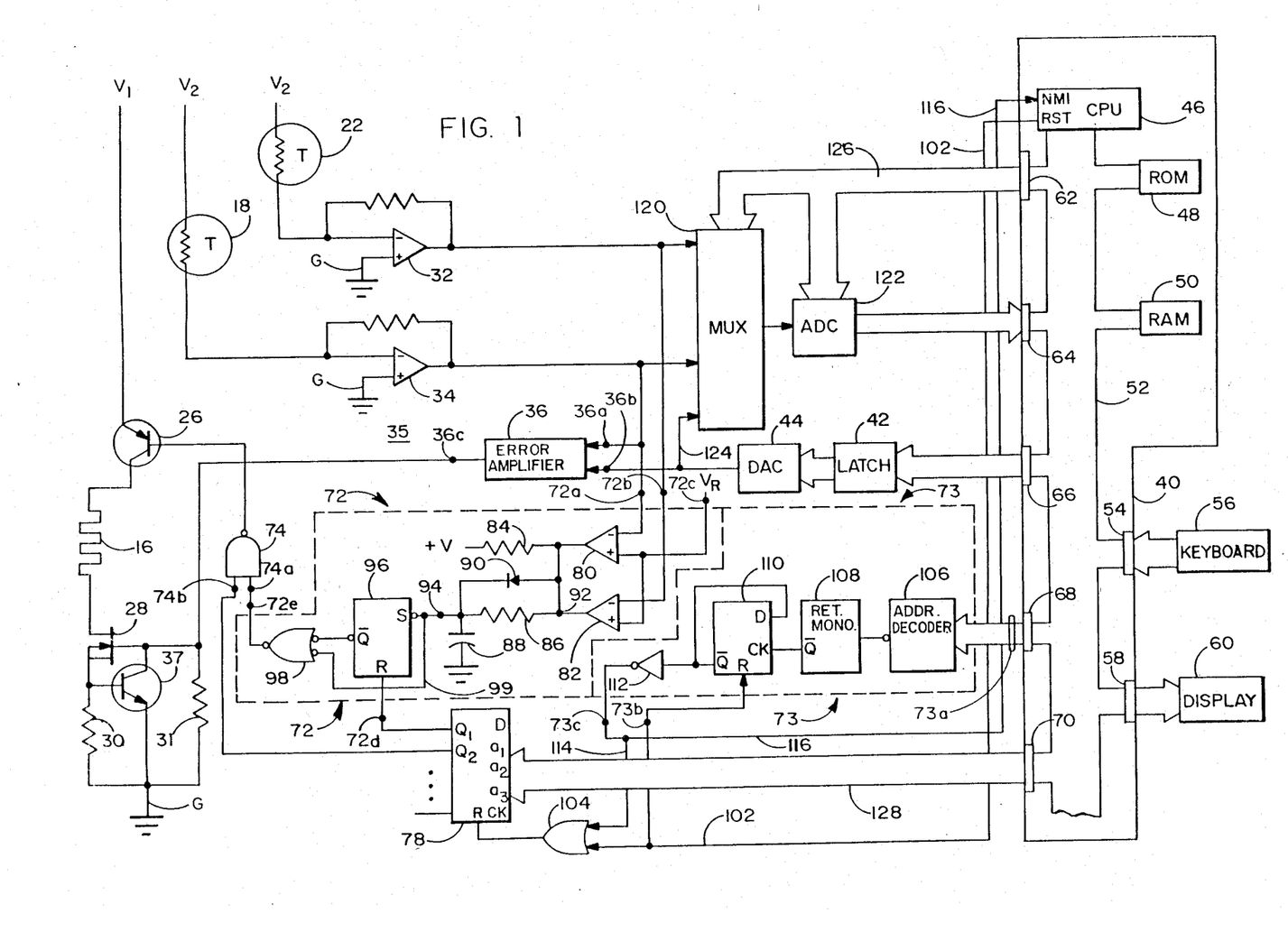
FIG. 1 is a combined block-schematic diagram of the preferred embodiment of the temperature control system of the present invention.
Figure 1A:
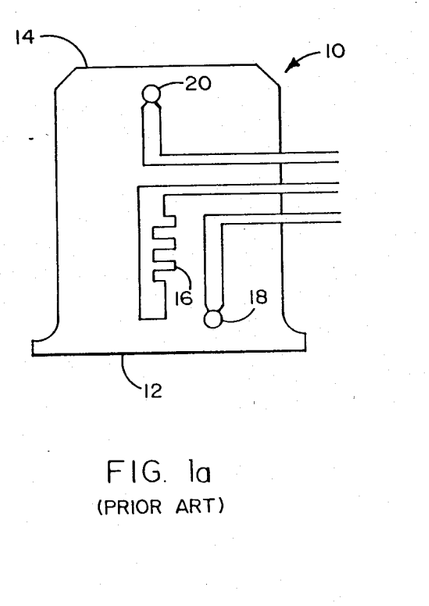
FIG. 1a shows, in simplified form, the internal arrangement of the temperature sensing elements of a cutaneous gas sensor of a type which is known in the art.

Referring to FIG. 1a, there is shown a simplified representation of a cutaneous gas sensor 10 of a type which is known in the art. In this sensor, the gas sensing electrodes and their associated components have been omitted for the sake of clarity. Sensor 10 has an inner surface 12 which is applied to the patient at the measurement site and an outer surface 14 which is exposed to the ambient air. Included within sensor 10 is a heating element 16 and first and second temperature sensing elements 18 and 20 which may comprise thermistors.

In operation, first sensing element 18 is used to sense the temperature of inner surface 12 (and therefore the temperature of the patient) and cause an external control circuit to vary the current through heating element 16 as necessary to maintain inner suface 12 (and the patient) at the desired setpoint temperature. Simultaneosly, second sensing element 20 is used to sense the temperature of outer surface 14. By sensing both the sensor-patient temperature and the ambient temperature, some known temperature control circuits attempt to determine the relative amounts of heat that are lost to the patient and to the ambient air. Since the amount of heat that is lost to the patient is dependent upon the rate of blood flow at the measurement site, these circuits are thought to provide an indirect measure of the rate of blood flow in the patient's skin.

Figure 1B:
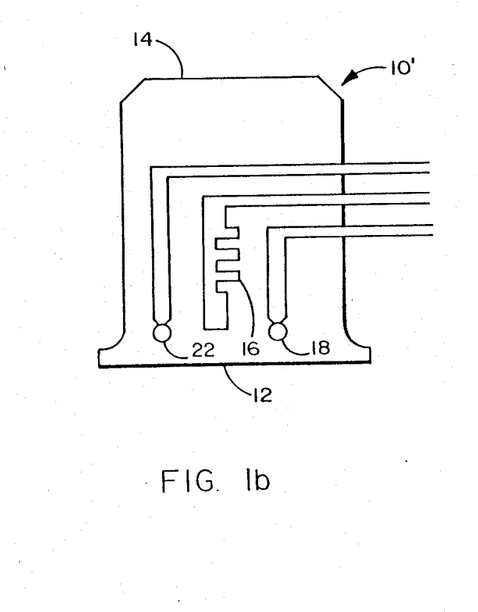
FIG. 1b shows, in simplified form, the internal arrangement of the temperature sensing elements of a cutaneous gas sensor of a type which is suitable for use with the present invention, and FIGS. 2a, 2b and 2c together comprise a flow chart which depicts the operation of the computer-controlled portion of the temperature control system shown in FIG. 1.

Referring to FIG. 1b, there is shown a simplified representation of a cutaneous gas sensor 10' of a type which is suitable for use with the present invention. Like sensor 10 of FIG. 1a, sensor 10' of FIG. 1b includes a heating element 16 and first and second temperature sensing thermistors 18 and 22. Unlike sensor 10, however, sensor 10' includes temperature sensing thermistors which are positioned so that they both measure the temperature at inner surface 12 of sensor 10'. Because thermistors 18 and 22 both sense the same temperature, one of them (18) can be used as a control thermistor to control the amount of current flow through heating element 16, while the other (22) is used as a monitoring thermistor to detect the presence of unacceptable sensor temperatures. It will therefore be seen that, while the gas sensors shown in FIGS. 1a and 1b both include two temperature sensing elements, these sensing elements have different positions and functions.

Referring to FIG. 1, there is shown a block-schematic diagram of the preferred embodiment of the temperature control system of the present invention. In this diagram heating element 16 and temperature sensing thermistors 18 and 22 of FIG. 1b have been drawn in schematic form to show their connections to the circuitry with which they operate. Heating element 16 is connected between a suitable d.c. voltage source V1 and system ground G through a switching transistor 26, a variable conducting transistor 28 and a resistor 30. Thermistors 18 and 22 are connected between a second d.c. voltage source V2 and system ground G via the virtual grounds at the inputs of operational amplifiers 32 and 34, respectively.

To the end that the conduction of transistor 28 may be controlled so that the actual temperature of sensor 10' remains substantially equal to the desired setpoint temperature, the circuit of FIG. 1 is provided with a closed loop temperature control circuit 35. This control circuit preferably includes control thermistor 18, amplifier 34, an error amplifier 36, heating element 16, transistor 28 and resistors 30 and 31. Circuit 35 may also include a current limiting circuit, here shown as the circuit including resistor 30 and a transistor 37, for limiting the magnitude of the current flow through heating element 16.

As shown in FIG. 1, amplifier 36 has a first input 36a which is connected to amplifier 34 to receive the actual temperature signal produced by control thermistor 18, an input 36b which is connected to receive a signal indicative of the desired setpoint temperature, and an output 36c which is connected to transistor 28. In operation, amplifier 36 generates an output signal which varies the flow of current through transistor 28 in accordance with the difference between the actual temperature signal at input 36a and the the desired temperature signal at input 36b, and thereby maintains the difference between those temperatures approximately equal to zero. The latter difference may be made even more nearly equal to zero by utilizing an error amplifier which includes integrating circuitry that causes amplifier 36 to control transistor 28 in accordance with the integral of the difference between the actual and desired temperature of sensor 10'. Because the operation of error amplifiers in closed loop temperature control circuits is well known, the operation of amplifier 36 and circuit 35 will not be described in detail herein.

The temperature at which circuit 35 operates is determined by a temperature setpoint signal that is generated by a digital microcomputer 40, and applied to amplifier input 36b through a storage device, which here takes the form of a suitable multi-bit latch 42, and a digital to analog converter or DAC 44. Because the signal is applied in this way, computer 40 is able to change the temperature setpoint of temperature control 35 by merely outputting a new digital signal to latch 42. Once this signal is stored in latch 42, however, computer 40 plays no continuing role in the operation of circuit 35. In other words, computer 40 sets the operating temperature for circuit 35, but is not otherwise necessary to maintain the operation thereof. The use of computer 40 as a temperature setting device for temperature control circuit 35 allows circuit 35 to continue to operate in the intended manner to maintain sensor 10' at the desired temperature, even if computer 40 itself should cease functioning.

Computer 40 may comprise a conventional single board microcomputer which includes a central processing unit or CPU 46, a program memory 48, part or all of which may be embodied in a read-only memory (ROM), a random access read/write memory (RAM) 50 and a suitable data/address bus 52. Computer 40 also includes a plurality of input/output (I/O) ports through which it may communicate with an operator or with its associated circuitry. These I/O ports include: (a) a port 54 which is connected to a set of manually operable switches, such as a keyboard 56, through which the operator may enter data or commands into the computer, (b) a port 58 which is connected to a suitable human readable display 60, such as a CRT or printer, through which the computer may communicate with the operator, and (c) ports 62-70 through which the computer may communicate with the remaining circuitry of FIG. 1. Additional ports may be provided for the reception of gas concentration data from sensor 10' or for the handling of signals from supporting circuits such as alarm circuits. Because these additional ports and circuits do not relate to the present invention, they are omitted for the sake of clarity.

As explained earlier, a patient may become severely burned if a failure in the temperature control circuitry causes the sensor to operate at a temperature which is not within safe operating limits. In order to prevent this from occurring, the circuit of FIG. 1 is provided with a switching device, here shown as a transistor 26, and with a plurality of protective circuits which are arranged to control the conductive state thereof. When the temperature control system is operating in the intended manner, these protective circuits allow transistor 26 to conduct. Under this condition the magnitude of the current through heater 16 is controlled by temperature control circuit 35. When, however, the system malfunctions or otherwise establishes an out of limits condition, one or more of these protective circuits will cause transistor 26 to turn off, thereby shutting off the flow of current through heater 16 without regard to the condition of temperature control circuit 35.

In the embodiment of FIG. 1, the temperature control system includes three different protective circuits. These include a first temperature monitoring circuit 72 which preferably utilizes hardwired circuitry, a second temperature monitoring circuit which preferably utilizes programmable circuitry such as computer 40, and a failure detecting circuit 73 which preferably utilizes hardwired circuitry. Of these, the first two protective circuits 72 and 40 carry out one or more tests to determine whether sensor 10' has malfunctioned or otherwise produced a temperature which is not within safe limits. The third protective circuit 73 carries out a test that identifies malfunctions in computer 40. These protective circuits are afforded joint control over the state of switching transistor 26 by connecting the same to transistor 26 via a NAND gate 74. The latter gate turns transistor 26 off when any of the protective circuits applies a low state voltage (i.e., a disable signal) to one or both of its inputs 74a and 74b.

NAND gate 74 may, if desired, be replaced by an equivalent multi-input analog circuit. Such a replacement may be desirable, in circuits in which voltage V1 is supplied by a battery, in order to allow voltage V1 to be made higher than that used with the remaining circuitry of FIG. 1. This higher voltage, in turn, allows the sensor to be operated for longer times between battery charges.

In the preferred embodiment, hardwired temperature monitoring circuit 72 turns off transistor 26 by applying a low state disable signal to gate 74 when the amplified output signal of one or both of thermistors 18 or 22 exceeds an overtemperature reference signal $V_R$. In addition, hardwired failure detecting circuit 73 turns off transistor 26 by applying a low state disable signal to gate 74, when computer 40 fails in such a way that it becomes unable to periodically apply a reset signal thereto. Since these conditions can occur either as a result of the failure of individual circuit components, such as amplifier 36, or as a result of the failure of computer 40 to properly execute its program, it will be seen that hardwired protective circuits 72 and 73 protect the patient against both hardware and software related malfunctions.

Programmable temperature monitoring circuit 40 turns off transistor 26, via gate 74 and a multi-bit addressable latch 78, when it detects the occurrence of any one or more of a plurality of unacceptable temperature conditions. In the preferred embodiment, these conditions are identified on the basis of the outcome of the following software implemented temperature tests: (i) do the temperatures indicated by the thermistors differ from one another by more than a predetermined amount?, (ii) does the average of the temperatures indicated by the thermistors differ from the setpoint temperature by more than a predetermined amount?, and (iii) does the temperature indicated by either thermistor exceed the maximum permissible sensor temperature? Since these temperature tests can be failed either as a result of the failure of individual circuit components, or as a result of the failure of computer 40 to properly execute its program, it will be seen that programmable monitoring circuit 40 also protects the patient against both hardware and software related malfunctions.

In order to accomplish its protective function, temperature monitoring circuit 72 is provided with inputs 72a and 72b which are connected to receive the amplified output signals of thermistors 18 and 22, respectively; an input 72c which is connected to receive suitable overtemperature reference signal $V_R$; an input 72d which is connected to receive a reset signal; and an output 72e which is connected to gate 74. In the embodiment of FIG. 1, circuit 72 includes a comparator network that comprises first and second comparators 80 and 82, a pull-up resistor 84, and an RC timing circuit that includes a resistor 86, a capacitor 88, and a diode 90. These devices are supplied with operating power from a suitable DC voltage source $+V$.

In operation, comparators 80 and 82 and pull-up resistor 84 cooperate to establish at a junction 92 a high state voltage which is approximately equal to voltage $+V$ when the output signals of thermistors 18 and 22 are both less than reference signal $V_R$, and to establish a low state voltage which is approximately equal to that of system ground G when either or both of the thermistor output signals exceed reference signal $V_R$. Thus, the presence of a high state voltage between junction 92 and ground G indicates a normal temperature condition at sensor 10', and the presence of a low state voltage therebetween indicates an overtemperature condition at sensor 10'.

The RC timining circuit including elements 86-90 establishes at a junction 94 a voltage which follows that at junction 92, but which undergoes high-to-low and low-to-high state voltage transitions which proceed at different rates. More particularly, resistor 86 and capacitor 88 serve to briefly delay the appearance of high-to-low state voltage transitions at junction 94. This is because such transitions will occur only after capacitor 88 discharges through resistor 86 for a long enough time. This brief delay is beneficial since it assures that transistor 26 is not shut off as a result of line voltage transients or induced voltage spikes. Diode 90 effectively short-circuits resistor 86 and allows capacitor 88 to charge rapidly in the presence of low-to-high state voltage transitions. This, in turn, assures that the latter transitions appear at junction 94 without any appreciable delay, and thereby further reduce the effect of line voltage transients or induced voltage spikes. Thus, the RC timing circuit assures that high-to-low state voltage transitions appear at junction 94 only when a real overtemperature condition occurs at sensor 10'.

In order to assure that transistor 26 is maintained in a non-conducting condition after the occurrence of a real overtemperature condition, junction 94 is connected to gate 74 through a suitable latch, here shown as a flip-flop 96. This flip-flop is set by a high-to-low state voltage transition at its set input S to produce a low-state voltage at the $\overline{Q}$ output thereof. This low state (disable) voltage, in turn, is applied to NAND gate 74, through a negative OR gate 98, to cause the output of gate 74 to assume its high state and thereby maintain transistor 26 in a non-conducting condition. Once established, this condition will persist unless and until a reset signal is applied to reset input R of flip-flop 96. (The condition under which such a reset signal is applied to flip-flop 96 will be discussed later.) Thus, monitoring circuit 72 affords latched overtemperature protection to the patient.

Temperature monitoring circuit 72 also includes a conductor 99 which connects junction 94 directly to negative OR gate 98. Low state signals applied to this conductor serve to turn-off transistor 26, via gates 98 and 74, only so long as they appear at junction 94. As a result, conductor 99 assures that circuit 72 is able to protect the patient against an overtemperature condition independently of the occurrence of any circuit conditions (such as start-up transients or circuit malfunctions) which may cause flip-flop 96 to be reset. Thus, control circuit 72 affords unlatched overtemperature protection to the patient.

In order to accomplish its protective function, failure detecting circuit 73 is provided with a multi-bit input 73a which is connected to output port 68 of computer 40, an input 73b which is connected to the reset (RST) output of CPU 46 through a conductor 102, and an output 73c which is connected to NAND gate 74 through OR gate 104 and addressable multi-bit latch 78. In the embodiment of FIG. 1, circuit 73 includes an address decoder 106, a retriggerable monostable multivibrator 108, a D-type flip-flop 110 and an inverter 112.

In operation, address decoder 106 serves to apply a low-state voltage to the input of multivibrator 108 during those times when a predetermined address appears on data-address bus 52. Provided that these times occur at intervals that are shorter than the time necessary for multivibrator 108 to reset itself, multivibrator 108 will remain set and thereby apply a continuous low-state voltage to the clock (CK) input of flip-flop 110. By programming computer 40 so that it generates the above address frequently enough, the presence of a continuous low-state voltage to the Q output of multivibrator 108 may be used as an indication that computer 40 is executing its program in the intended manner. Conversely, the appearance of a high stage voltage at the $\overline{Q}$ output of multivibrator 108 may be used as an indication that computer 40 is not executing its program in the intended manner.

If computer 40 is operating normally, multivibrator 108 will be unable to apply to flip-flop 110 the low-to-high state voltage transition that is necessary to change to the state thereof. As a result, the $\overline{Q}$ output of flip-flop 110 remains in the high state which it was forced to assume by a reset signal applied thereto by CPU 46, via conductor 102, at the time of start up. As long as this condition exists, inverter 112 will apply a continuous low-state voltage to OR gate 104, via conductor 114, and to the non-maskable interrupt (NMI) of CPU 46, via conductor 116. Since this low state voltage cannot cause latch 78 to apply a low-state voltage to gate 74, and cannot cause an interrupt of CPU 46, the temperature control system will maintain conduction in transistor 26, unless the latter is turned off by one of the other protective circuits, such as circuit 72.

If, on the other hand, computer 40 fails to operate normally, it will be unable to apply to multivibrator 108 the signals necessary to prevent the latter from changing the state of flip-flop 110. As a result, flip-flop 110 will apply a low-state voltage to inverter 112. The resulting high-state voltage at the output of inverter 112 will, in turn, cause OR gate 104 to reset latch 78 and thereby turn off transistor 26 by applying a disable signal to input 74b of gate 74. It will be understood, however, that it is not essential that flip-flop 110 turn off transistor 26 by resetting latch 78. It may, for example, turn off transistor 26 by applying a disable signal to an additional flip-flop having an output that is connected to one input of a three-input version of gate 74.

The high-state voltage at the output of inverter 112 will also activate the NMI input of CPU 46, via conductor 116. In the preferred embodiment, the activation of this input will direct the computer 40 to a part of its program that causes it to take action to protect the patient. This action preferably includes the outputting to DAC 44 of a reduced temperature setpoint signal, i.e., a setpoint signal which will cause amplifier 36 to shut off transistor 28, and the outputting of a signal which will notify the operator of a failure. (As will be explained more fully later, this reduced setpoint signal is also outputted to DAC 44 in response to the occurrence of any of a number of other unacceptable temperature conditions.) The shutoff of transistor 28 provides a further level of patient protection by assuring that no current will flow through heater 16 even if transistor 26 and/or gate 74 should malfunction.

From the foregoing, it will be seen that protective circuits 72 and 73 are adapted to shut-off the flow of heater current, in response to the occurrence of any one or more of a plurality of malfunctions in either the hardware or software controlled portions of the temperature control system of FIG. 1, independently of the operability of computer 40.

While protective circuits 72 and 73 are preferably implemented with the discrete, hardwired circuit elements shown in FIG. 1, they may also be implemented with program controlled circuitry, i.e., additional programmed microcomputers. If the latter are used, however, they should be connected and programmed so that, like their hardwired counterparts, they can continue to perform their protective function independently of the proper functioning of computer 40. Their data/address buses should not, for example, be directly connected to the data/address bus of computer 40. In such usage, these additional microcomputers comprise program controlled equivalents of hardwired circuits 72 and 73. Because of this equivalency, embodiments which utilize such addititional microcomputers will not be described in detail herein.

As explained earlier, computer 40 serves as a second temperature monitoring circuit by executing a program which performs the three above-mentioned temperature tests. The program which computer 40 uses to carry out these tests will be described later in connection with the flow chart of FIG. 2a. The manner in which computer 40 receives the information necessary to apply these tests, and the manner in which computer implements the results of these tests will now be described in connection with the circuit of FIG. 1.

In the embodiment of FIG. 1, computer 40 receives the output signals of thermistors 18 and 22 through a suitable multiplexer 120 and an analog to digital converter 122. Multiplexer 120 may also be connected to the output of DAC 44, through a conductor 124, to enable computer 40 to read the temperature setpoint signal which is actually being applied to error amplifier 36. Reading the latter voltage enables the computer to automatically calibrate DAC 44, as will be explained more fully presently. In order to assure that the multiplexed temperature information is provided to computer 40 at the proper times, computer 40 controls the operation of multiplexer 120 and analog to digital converter 122, via port 62 and a set of conductors 126. Because the operation of multiplexers and analog to digital converters are well known to those skilled in the art, the operation thereof will not be described in detail herein.

If, after processing the thermistor output signals, computer 40 determines that sensor 10' is not functioning within safe limits, it will take action to protect the patient. A first part of this protective action includes applying to multi-bit addressable latch 78, over a set of conductors 128, a digital signal which will cause output $Q_2$ thereof to apply a latched low-state voltage to input 74b of gate 74. The effect of this action is to shut off transistor 26 and hold the same in a non-conducting state. A second part of this protective action includes applying to latch 42 a digital signal which will cause DAC 44 to apply a predetermined reduced temperature setpoint signal (such as one that produces a temperature of 37° C.) to summing amplifier 36. The effect of this action is to partly or completely shut off the flow of current through transistor 28. Thus, the computer is able to limit or stop the flow of current through the devices connected to both ends of heater 16, and thereby protect the patient even if one of transistors 26 or 28 should fail.

Because of the number and sensitivity of the tests that are used to identify unacceptable operating conditions, the circuitry of FIG. 1 may exhibit a tendency to shut off the flow of current through heater 16 during the course of normal temperature transients. When, for exaple, the system is first turned on, temperature transients may cause the circuit of FIG. 1 to become latched into a condition in which transistor 26 is maintained in a non-conducting state, even though the patient is not in any danger of being burned. In order to prevent this, computer 40 is given the ability, at the time of turn on, to reset latch 96 and to temporarily disable the above-mentioned software implemented temperature tests. Even when it does so, however, the patient is protected by other parts of the circuitry of FIG. 1. Thus, the temperature control system of FIG. 1 accommodates the need for patient safety without exhibiting a tendency to "latch up".

In the embodiment of FIG. 1, the computer's ability to prevent the latch up of the system at turn on is exercised via digital signals that are applied to multi-bit addressable latch 78. By setting output $Q_1$ of latch 78 to its high state, for example, flip-flop 96 is reset and thereby initially caused to apply a high state (enable) signal to input 74a of gate 74. Similarly, by setting output $Q_2$ of latch 78 to its high state, latch 78 is caused to apply a high state (enable) signal to input 74b of gate 74. Note, however, that monitoring circuit 72 can terminate this enabled condition by producing a low state signal at junction 94, and that circuit 73 can terminate this enabled condition by resetting latch 78 via conductor 114 and gate 104. Thus, the system is prevented from latching up at the time of turn on without creating a risk of patient harm.

The overall start up of the system of FIG. 1 will now be described. During this start up computer 40 first forces transistor 26 to assume its non-conducting state, and then outputs a sequence of signals which allows the circuitry of FIG. 1 to start up in an orderly manner. In the preferred embodiment computer 40 holds transistor 26 in a non-conducting state by outputting a high state reset signal from the RST output of CPU 46 for a predetermined time. This reset signal holds transistor 26 in its non-conducting state by resetting latch 78, through OR gate 104, and thereby assuring that a low state voltage is maintained at input 74b of gate 74. At the same time, this reset signal is applied to reset input R of flip-flop 110 to assure that the latter begins its operation in a state that is indicative of normal operation in computer 40.

At the end of the reset signal, the high state voltage is removed from latch 78 and flip-flop 110. The latter will, however, remain in their reset states unless set by some subsequently applied signal. If computer 40 is operating normally, it will then begin to periodically retrigger multivibrator 108 via decoder 106 to maintain the reset state of flip-flop 110. Computer 40 will then start up the remaining circuitry of FIG. 1 by:

(a) outputting to DAC 44 a digital signal that specifies the desired setpoint temperature;

(b) outputting to latch 78 via conductors 128 a signal which will set output $Q_1$ thereof into its high state; the latter signal resets flip-flop 96 and thereby assures that the circuit of FIG. 1 does not start in a latched up condition;

(c) disabling the software implemented temperature tests for the expected duration of the start-up temperature transient and outputting to latch 78 via conductors 128 a signal which will set output $Q_2$ thereof into its high state; this signal has the effect of enabling gate 74 and thereby turning on the flow of current through transistor 26 and heater 16.

After enough time has passed for the start-up temperature transient to have terminated, computer 40 will enable the software implemented temperature tests, and thereby restore its ability to cause latch 78 to apply a latched disable signal to gate 74. When this occurs, the circuitry of FIG. 1 will be fully operational and will operate in the previously described manner unless it is shut off either by its operator, or as a result of the operation of one of protective circuits 72, 73 or 40.

Unlike monitoring circuit 40, monitoring circuit 72 is not disabled during the start-up temperature transient. In spite of this, circuit 72 will not ordinarily cause the circuit of FIG. 1 to apply a latched disable signal to gate 74 during start up. This is because the magnitude of overtemperature reference signal $V_R$ is set at a sufficiently high (but still safe) value that it will not be exceeded during the start-up temperature transient. In other words, monitoring circuit 72 is preferably designed so that it is less sensitive to excessive temperatures in sensor 10' than monitoring circuit 40.

It will be understood, however, that, if desired, overtemperature reference signal $V_R$ may be made low enough that circuits 72 and 40 are equally sensitive to excessive temperatures in sensor 10'. In the latter event, flip-flop 96 should be held in a reset condition during the start-up temperature transient. This reset condition may be maintained by outputting to latch 78 a signal which will cause the output of $Q_1$ thereof to remain set during the start up temperature transient.

The temperature control system of the invention is also arranged to prevent its circuitry from becoming latched up as a result of the temperature transients that normally occur after changes in the setpoint temperature. This is accomplished in generally the same manner as the prevention of latch up during start up, namely: the disabling of the software implemented temperature tests for the duration of the expected transient, coupled with the setting of output $Q_2$ of latch 78 to its high state. Since the duration of a temperature transient of this type is ordinarily less than that of the start up transient, the time period during which the software implemented temperature tests are disabled on changes in the setpoint temperature is preferably shorter than the time period during which these tests are disabled on start up.

The ability of the system to avoid becoming latched during normal temperature transients is further enhanced by current limiting transistor 37. This is because transistor 37 imposes a ceiling on the current through heating element 16 by lowering the voltage on the gate of transistor 28 in response to the flow of current through series connected resistor 30. As a result, the tendency of the sensor temperature to overshoot the desired final temperature during temperature transients is substantially eliminated. A particularly desirable feature of this current limiting arrangement is that it reduces sensor temperature overshoot without creating a need to place a high wattage current limiting resistor in series with heating element 16. Such a high wattage resistor can waste energy and thereby greatly reduce the time that a battery operated cutaneous gas monitor can operate between battery charges.

Figure 2A:
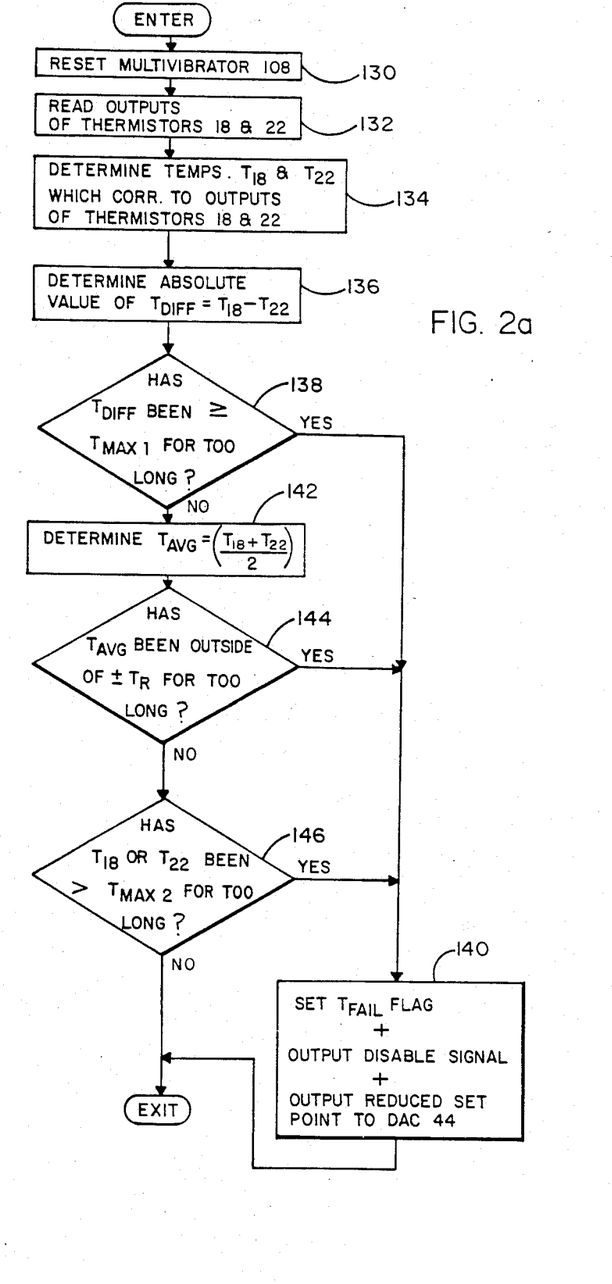

The program which computer 40 uses to determine whether sensor 10' is operating at an accceptable temperature is best understood with reference to the following description of the flow chart of FIG. 2a. Upon entering the portion of the program shown in FIG. 2a, the computer first encounters a block 130 which causes it to output the address necessary to reset multivibrator 108 and thereby prevent circuit 73 from determining that the computer has malfunctioned. Computer 40 then proceeds to blocks 132 and 134 which cause it to read the output signals of control and monitoring thermistors 18 and 22, and determine the temperatures $T_{18}$ and $T_{22}$ which correspond to those output signals. This determination may, for example, be made by referring to a look-up table which contains the thermistor temperatures that correspond to particular output signals. Alternatively, the computer may solve a power series equation which relates the output signal of the thermistor to its temperature. Other procedures for determining the thermistor temperatures will be apparent to those skilled in the art.

After determining temperatures $T_{18}$ and $T_{22}$, the computer is directed to a block 136 which causes it to determine the absolute value of the temperature difference $T_{DIFF}$ between them, and to a block 138 which causes it to compare temperature difference $T_{DIFF}$ to a predetermined maximum acceptable temperature $T_{MAX1}$. If temperature difference $T_{DIFF}$ exceeds temperature $T_{MAX1}$ for more than a suitable predetermined time, such as several seconds, it is known that the performance of one of these thermistors has deteriorated with respect to the other in such a way that sensor 10' is no longer functioning in an acceptable manner. Under this condition, the computer is directed to a block 140 which causes it to take the actions necessary to protect the patient. These actions include (a) setting a temperature fail flag to record the occurrence of the failure, (b) outputting a disable signal to gate 74 via latch 78, and (c) outputting a reduced temperature setpoint signal to DAC 44.

If, on the other hand, temperature difference $T_{DIFF}$ has not exceeded temperature $T_{MAX1}$ for more than the predetermined time, the computer is directed to a block 142. In the latter block the computer is directed to determine the average temperature $T_{AVG}$ indicated by the thermistors, and then to proceed to a block 144 which causes it to determine whether average temperature $T_{AVG}$ has varied outside of a predetermined range of temperatures $\pm T_R$, centered on the desired temperature, for more than a predetermined suitable time. If average temperature $T_{AVG}$ has varied outside of that range for more than the permitted time, it is known that one or both of the thermistors are no longer functioning in an acceptable manner. Under this condition, the computer is again directed to block 140 to take the previously described actions to protect the patient.

If average temperature $T_{AVG}$ has not varied outside of temperature range $\pm T_R$ for more than the permitted time, computer 40 is directed to a block 146. In the latter block the computer is directed to determine whether temperatures $T_{18}$ and $T_{22}$ have exceeded the maximum sensor temperature $T_{MAX2}$ for more than a suitable predetermined time. If that determination indicates that temperature $T_{MAX2}$ has been for more than the permitted time, computer 40 is again directed to block 140 to take the previously described actions to protect the patient. If the determination indicates that $T_{MAX2}$ has not been exceeded for more than the permitted time, the computer is directed to exit the flow chart of FIG. 2a and proceed with the execution of the remainder of the program.

From the foregoing, it will be seen that computer 40 is programmed to take action to protect a patient upon the occurrence of any one of a plurality of program defined unacceptable temperature conditions. While the tests performed via decision blocks 138, 144 and 146 of FIG. 2a are regarded as the most desirable combination of tests for the presence of such conditions, it is recognized that other tests or combination of tests may be used for this purpose. An unacceptable condition may, for example, be defined in terms of a predetermined rate of change in a thermistor output signal, or in terms of whether each thermistor output signal is within a predetermined range of temperatures centered on the set temperature. Accordingly, these and other combinations of tests will be understood to be within the contemplation of the present invention.

Together with protective circuits 72 and 73, protective circuit 40 provides multi-level protection for a helpless patient. A malfunction in circuit 72 or 73, for example, will be prevented from injuring a patient by the action of circuit 40. Similarly, a malfunction in circuit 40 will be prevented from injuring a patient by the action of circuit 72 and/or 73.

Still further levels of protection are provided by redundancies within the protective circuits. If, for example, one of the three above-mentioned tests should fail to identify an unacceptable temperature condition, the flow of heater current may be shut off as a result of conditions identified by either of the remaining two tests. Similarly, if one of the thermistors or comparators of circuit 72 should fail, the flow of heater current may be shut off by the other thermistor or comparator thereof.

In addition to the above-described protective circuitry, the temperature control system of the invention includes circuitry for accelerating the warm-up of the part of the patient to which the sensor is applied (i.e., the measurement site) and thereby reducing the time necessary for the sensor to provide usable data after first being applied to the patient. The manner in which this circuitry operates is most easily understood in the context of the overall operation of the temperature control system of FIG. 1. This overall operation will now be discussed in connection with the flow charts of FIGS. 2b and 2c.

Figure 2B:
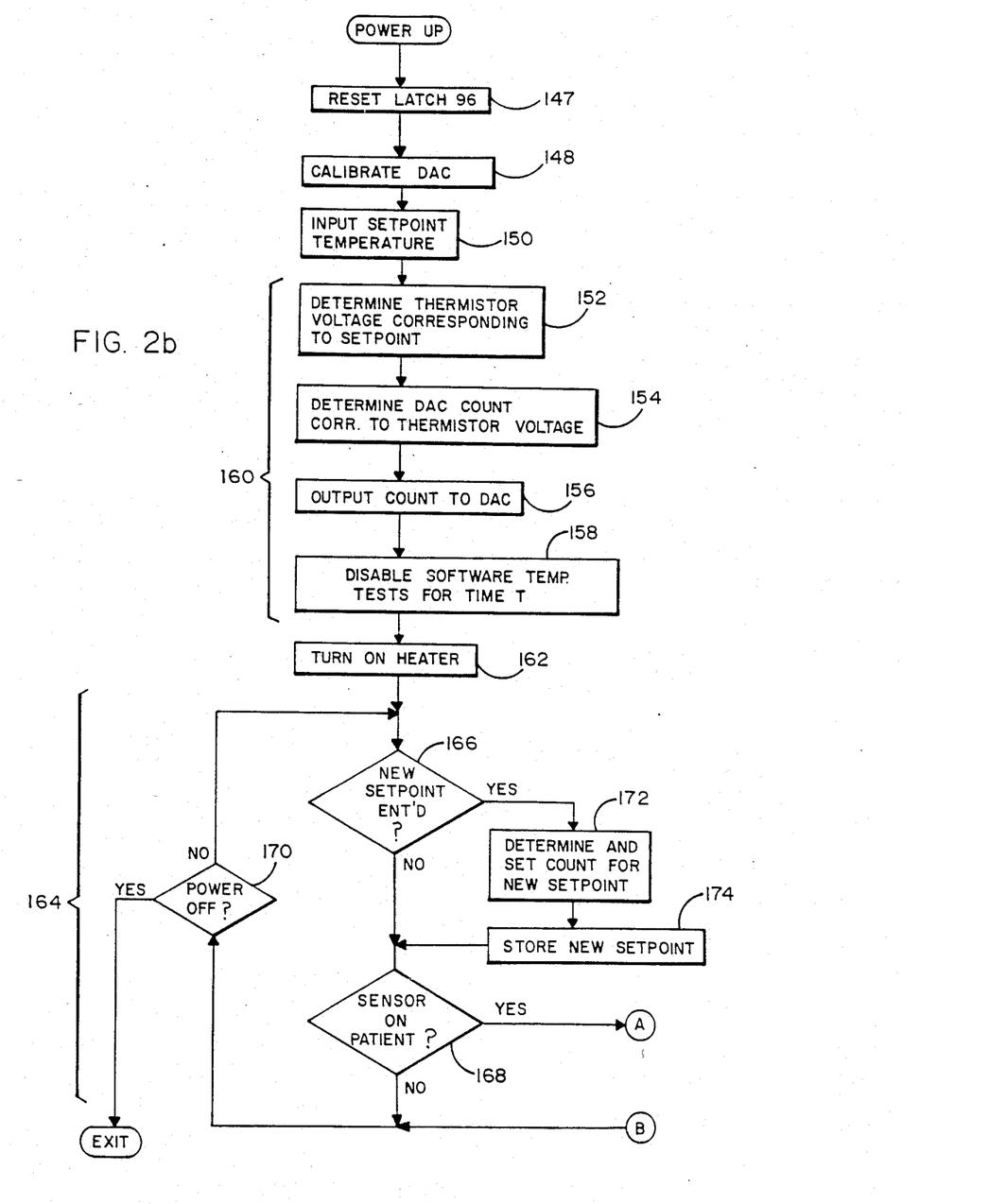

After being turned on, computer 40 will first encounter a block 147 which causes it to set the $Q_1$ output of latch 78 and thereby reset latch 96. The resetting of the latter assures that protective circuit 72 does not start up in a condition in which it applies a latched disable signal to gate 74.

Computer 40 then proceeds to a block 148 which causes it to calibrate DAC 44 of FIG. 1. In doing so, computer 40 determines the numerical values of the digital signals (hereinafter referred to as "counts") which must be output through port 66 in order to produce a particular analog voltage at the output of DAC 44. This calibration is preferably accomplished by outputting an all 0's count to DAC 44 and reading the resulting analog voltage via conductor 124 and analog to digital converter 122, and then outputting an all 1's count to DAC 44 and again reading the resulting analog voltage via conductor 124 and analog to digital converter 122. Based on these two voltages, computer 40 establishes a linear equation which yields the count which must be output to DAC 44 to produce any desired analog output voltage at the output thereof. Calibrating the DAC in this manner is desirable because it allows the circuitry to provide an accurate temperature setpoint signal from an inexpensive (non-precision) DAC.

After calibrating DAC 44, the computer is directed to a block 150 which causes it to input the desired setpoint temperature. This setpoint temperature may be a temperature requested by the operator through keyboard 56 or a previously selected setpoint which is stored in RAM 50 or ROM 48.

After exiting block 150, computer 40 proceeds to a series of blocks numbered 152 through 158 which together comprise a subroutine 160 that causes the computer to determine and output to DAC 44 the count necessary to establish the desired setpoint temperature. As will be apparent from the following description, this subroutine is executed at a number of different points in the flow chart of FIGS. 2b and 2c. The execution of this subroutine will be indicated by the occurrence of each block labeled "determine and set count for new setpoint".

Upon entering subroutine 160, computer 40 first encounters a block 152 which directs it to determine the thermistor output signal which corresponds to the desired setpoint temperature. This determination may, for example, be made by referring to a look-up table which contains the output signals produced by the thermistors at various temperatures. Alternatively, the thermistor output voltage may be determined from a previously stored power series equation which gives the temperatures at which the thermistors produce various output signals. Because these and similar determinations are well known to those skilled in the art, they will not be described in detail herein.

After determining the thermistor output signal which corresponds to the desired setpoint temperature, the computer is directed to a block 154 which causes it to determine the count which must be output to DAC 44 to produce the thermistor output signal that is associated with the desired setpoint temperature. This determination is made by solving the equation that was produced during the calibration of DAC 44 (block 148) for the count which will cause DAC 44 to apply the proper analog voltage to summing amplifier 36.

After making these determinations, the computer is directed to a block 156 which causes it to output the above count to DAC 44. The computer then proceeds to a block 158 which causes it to disable the software implemented temperature tests described in connection with the flow chart of FIG. 2a for a predetermined suitable time which, in the case of start-up, is preferably three minutes. As explained earlier, the disabling of these tests prevents the circuit of FIG. 1 from latching up in response to normal start up temperature transients, without completely taking away the ability of the circuit of FIG. 1 to respond to unacceptable temperature conditions within sensor 10'.

After exiting subroutine 160, computer 40 proceeds to a block 162 which causes it to output to latch 78 a signal which sets output $Q_2$ high and thereby enables input 74b of gate 74. Provided that the temperature of sensor 10' is found acceptable by monitoring circuit 72, this signal has the effect of turning on transistor 26 and permitting current to flow through heater 16. Once this occurs, closed loop temperature control circuit 35 will take over to cause sensor 10' to quickly reach a temperature that is equal to the desired setpoint temperature. In order to avoid a latched up condition, this temperature should be reached before the software implemented temperature tests are enabled by computer 40. If the latter result does occur, the temperature of sensor 10' will be maintained at the desired value, with no further involvement by computer 40, unless the operator changes the operation of the system via keyboard 56, or unless a malfunction or out of limits temperature condition occurs.

After sensor 10' is at the desired temperature, computer 40 will continue to test for operator initiated changes in the system by repeatedly executing the loop indicated by the number 164 in FIG. 2b. This loop, which may be referred to as the "off-patient" monitoring loop, includes decision blocks 166 through 170 and blocks 172 and 174. As the computer enters this loop, it first encounters a decision block 166 which causes it to scan keyboard 56 to determine whether the operator has requested a change in the setpoint temperature. If no new setpoint temperature has been requested, computer 40 proceeds to decision block 168 which causes it to determine whether the operator has indicated that he is placing or has placed the sensor on the patient. If the operator has so indicated, the computer is directed to block 170 which causes it to determine whether the operator has turned the system off. If he has, the computer will proceed to shut down the system by executing a suitable shutdown routine. Otherwise, the computer is directed to return to block 166 to re-execute off-patient loop 164.

If, on encountering block 166, the computer determines that the operator has entered a new setpoint temperature, it is directed to a block 172 which causes it to execute a subroutine which is the same as subroutine 160, except that it includes a test disable period, such as one minute, which is appropriate for setpoint temperature changes. As this occurs, computer 40 outputs the new setpoint temperature and, on encountering block 174, stores that temperature for later use. Unless the operator has indicated that the sensor is being or has been placed on the patient, however, the computer will not be directed to exit off-patient loop 164. The computer will therefore continue to execute this loop, including any requested setpoint temperature changes, until a request to the contrary occurs.

Figure 2C:
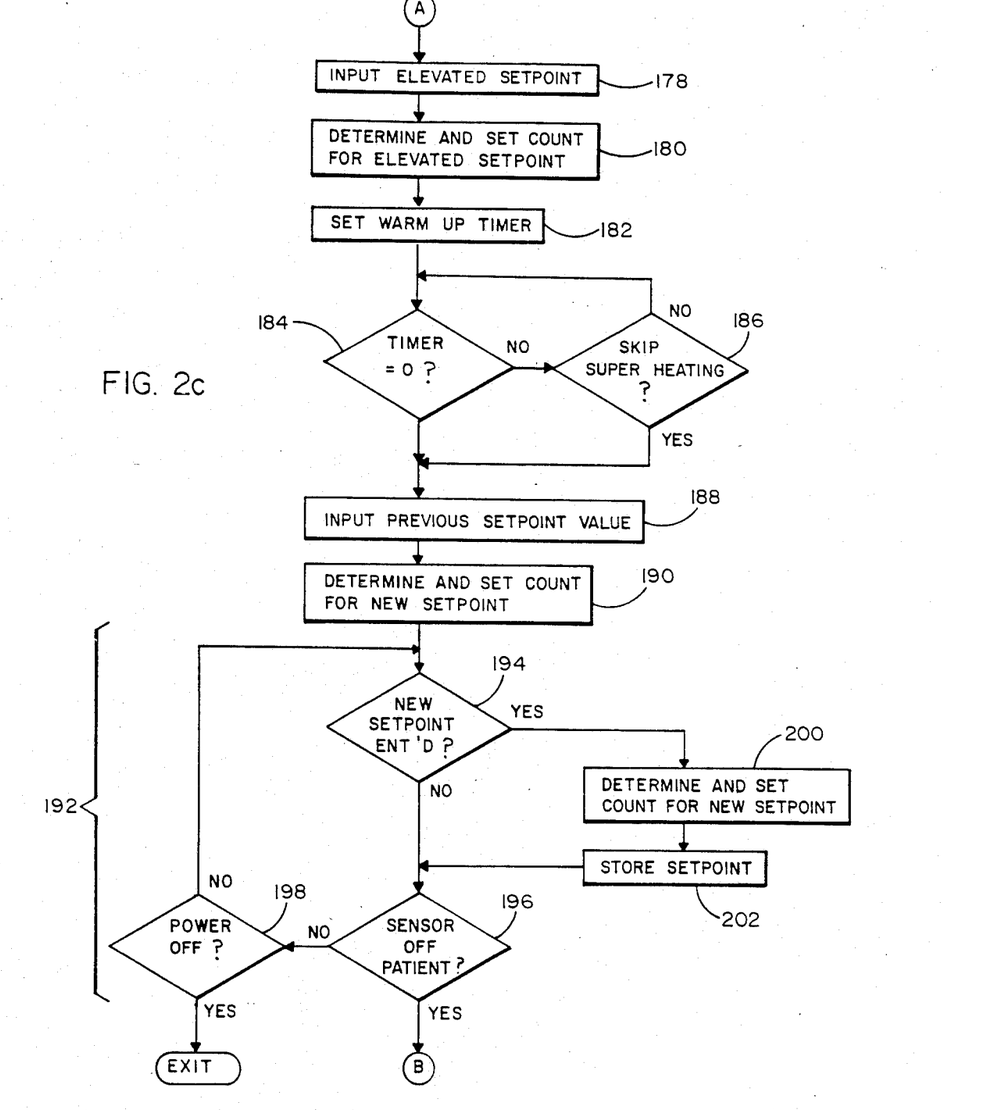

Once the operator places the sensor on the patient, and notifies the computer that he has done so, the computer will be directed to exit off-patient loop 164 and proceed (via connector A) to the flow chart of FIG. 2c. Because the temperature of sensor 10' will ordinarily be at a temperature, such as 42° C., which is several degrees above the normal human body temperature of 37° C., the placement of the sensor on the patient will be accompanied by a drop in the sensor temperature. This drop in temperature will, in turn, cause an increase in the magnitude of the error signal at output 36c of amplifier 36 and of the current flowing through heater 16. Prior to the present invention, this increase in current would gradually cause the sensor to warm the part of the patient under the sensor to the desired operating temperature of 42° C. Ordinarily, this warming took about 30 minutes. Since no useful data was produced during these 30 minutes, this warm-up period was largely wasted.

In accordance with the present invention, the duration of the warm-up period is reduced by elevating the setpoint temperature, for a predetermined time, such as four minutes, in order to temporarily superheat the sensor and thereby increase the rate at which heat may be supplied to the patient. The manner in which this is accomplished will now be described in connection with the flow chart of FIG. 2c.

Upon entering the flow chart of FIG. 2c (at connector A), the computer first encounters a block 178 which causes it to input the elevated setpoint (or superheating) temperature that has been selected for use during the warm-up period. For safety reasons, this elevated setpoint temperature preferably has a fixed value, such as 44° or 45° C., which is not subject to change by an operator. Having a fixed elevated setpoint temperature assures that the operator cannot inadvertently set this temperature to a value which can injure the patient. Upon inputting this elevated setpoint temperature, the computer proceeds to a block 180 which causes it to determine and set into DAC 44 the count necessary to establish the elevated setpoint temperature. This is accomplished by executing a subroutine which is the same as subroutine 160, except that it includes the same one minute test disable period that is used with other setpoint temperature changes.

Once the count associated with the elevated setpoint temperature has been outputted to DAC 44, the computer is directed to a block 182 which causes it to set a timer (preferably a software timer) which sets the above-mentioned four minute warm-up period. The computer then proceeds to a decision block 184 which causes it to repeatedly test for the elapse of the warm-up period. If desired, a decision block 186 may be inserted to give the operator the option of skipping the superheating process and proceeding with the execution of the remainder of the program. The skipping of the superheating process is desirable in cases in which the patient has a higher than normal body temperature, or in which the sensor is being re-applied to an already heated measurement site.

After the warm-up period has elapsed, decision block 184 directs the computer to blocks 188 and 190. In block 188 the computer is caused to input the setpoint temperature which was used (and stored) prior to the beginning of the superheating process. Block 190 then causes the computer to determine and set into DAC 44 the count necessary to re-establish that prior setpoint temperature. This is done by executing a subroutine which is the same as subroutine 160, except that it includes the one minute test disable period that is used with setpoint temperature changes. Once the test disable period that is associated with this subroutine has elapsed, sensor 10' will again be operating at its original setpoint temperature with all of protective circuits 72, 73 and 40 fully enabled.

In view of the foregoing, it will be seen that the temperature control system of the invention is adapted to automatically change its closed loop setpoint temperature, in accordance with a predetermined schedule, to substantially reduce the time delay between the application of the sensor to the patient and the production of useful data. In addition, the temperature control system of the invention accomplishes this result without either depriving the patient of the benefits of the above-described protective circuits, or allowing the system to be latched into a disabled condition by normal temperature transients.

After exiting block 190, the computer is directed to a monitoring loop 192 which is similar to loop 164 of FIG. 2b, except that it is associated with an on-patient rather than an off-patient operating condition. This "on-patient" loop includes blocks 194 through 202 which correspond to blocks 166 through 174, respectively, of off-patient loop 164. In operation, this monitoring loop serves to test for and implement operator-requested temperature changes or shut-downs. Unlike off-patient monitoring loop 164, however, on-patient monitoring loop 192 is exited when the sensor is removed from the patient, rather than applied to the patient. As indicated by connector B of FIG. 2c, notifying the computer that the sensor has been removed from the patient causes the computer to return to off-patient loop 164, without performing any steps that correspond to those performed before the entry of the on-patient loop.

While the execution of the temperature test program of FIG. 2a has been described separately from the execution of the start up and temperature control program of FIGS. 2b and 2c, these programs are preferably executed substantially simultaneously. One way of accomplishing this substantially simultaneous execution is to interleave the execution of these two programs. The programs shown in FIGS. 2a and 2b and 2c may, for example, be executed during alternating time periods. Provided that these time periods alternate frequently enough, and that provision is made for storing the status of the two programs before each alternation, the objectives of both programs may be achieved simultaneously without adversely affecting the objectives of either. Since the interleaved execution of multiple programs is well known to those skilled in the art, it will not be described in detail herein.

In view of the foregoing, it will be seen that a temperature control system constructed in accordance with the present invention includes two important improvements over previously known temperature control systems for cutaneous gas sensors. Firstly, the control system includes multi-level protective circuitry which assures that a patient will not be injured as a result of single hardware or software malfunctions. Secondly, the temperature control system of the invention includes temperature setting circuitry which is adapted to automatically change the setpoint temperature of the sensor, according to a predetermined schedule, when the sensor is switched from an off-patient to an on-patient operating condition, thereby greatly reducing the time that has been necessary to warm the measurement site to a temperature at which useful data can be produced. Together these improvements enhance the utility, safety and convenience of cutaneous gas sensing instruments.

What is claimed is:

1. A cutaneous gas monitoring system comprising;
   a sensor;
   a first sensing means for generating a first output signal indicative of the actual temperature of the sensor;
   a heating means for elevating the temperature of the sensor;
   a control means for establishing a temperature setpoint signal variable between, at least, a first and a second temperature, and indicative of a desired temperature of the sensor, wherein the temperature setpoint signal is established at the second temperature for a predetermined length of time after the sensor is placed on a patient and the temperature setpoint signal is established at the first temperature after the elapse of the predetermined length of time, wherein the first temperature is lower than the second temperature, and for regulating the heating means in accordance with the difference between the output signal of the sensing means and the temperature setpoint signal;
   means connected to the first sensing means which functions to reduce the temperature of the sensor after the first output signal exceeds a predetermined value.

2. The monitoring system of claim 1 wherein the means which functions to reduce the temperature of the sensor disables the heating means.

3. The monitoring system of claim 1 wherein the means which functions to reduce the temperature of the sensor reduces the temperature setpoint signal.

4. The monitoring system of claim 1 wherein the means which functions to reduce the temperature of the sensor is connected to a second sensing means for generating a second output signal indicative of the actual temperature of the sensor.

5. The monitoring system of claim 4 wherein the means which functions to reduce the temperature of the sensor further comprises circuits for carrying out a test, using the first and second output signals, for determining whether both sensing means are functioning properly.

6. The monitoring system of claim 4 wherein the means which functions to reduce the temperature of the sensor operates when the difference between the first and second output signals exceeds a predetermined amount.

7. The monitoring system of claim 4 wherein the means for reduucing the temperature of the sensor operates after the second output signal exceeds a predetermined amount.

8. The monitoring system of claim 1 wherein the control means comprises a programmable microprocessor that is programmed for establishing the temperature setpoint signal and regulating the heating means.

9. The monitoring system of claim 8 further comprising a failure detecting means which functions to reduce the temperature of the sensor when a program of the microprocessor fails to properly execute.

10. The monitoring system of claim 9 wherein the failure detection means includes resettable means which functions to reduce the temperature of the sensor unless the microprocessor periodically resets the resettable means.

11. The monitoring system of claim 1 further comprising an override means preventing the means which functions to reduce the temperature of the sensor from operating if the first output signal exceeds the predetermined value during a temperature transient.

12. The monitoring system of claim 11 wherein the temperature transient results from changing the temperature setpoint signal.

13. The monitoring system of claim 11 wherein the temperature transient results during the start-up of the monitoring system.

14. A cutaneous gas monitoring system for measuring a partial pressure of a constituent gas comprising a heating element, and a temperature sensing element for producing an output signal indicative of the actual temperature of a cutaneous gas sensor, and a temperature control means connected to the heating element and to the temperature sensing element for controlling the flow of current through the heating element in accordance with the difference between the output signal of the sensing element and a variable temperature setpoint signal, and a switching means connected to the heating element responsive to a disable signal for limiting the flow of current through the heating element, and a temperature setting means connected to the temperature control means which establishes the temperature setpoint signal at a first temperature when the sensor measures the partial pressure of the constituent gas and which establishes the temperature setpoint signal at a second temperature for a predetermined length of time prior to when the sensor measures the partial pressure of the constituent gas wherein the first temperature is lower than the second temperature, and a disabling means connected to the sensing element and to the switching means for establishing the disable signal after the output signal of the sensing element exceeds a predetermined value.

15. The monitoring system of claim 14 wherein the temperature setting means and the temperature control means comprise a programmable microprocessor that is programmed for establishing the temperature setpoint signal and controlling the flow of current through the heating element.

* * * * *